United States Patent [19]

Esanu

[11] Patent Number: 4,782,068
[45] Date of Patent: Nov. 1, 1988

[54] NEW QUINOLINE DERIVATIVES, THEIR PREPARATION AND THERAPEUTIC COMPOSITIONS CONTAINING THE SAME

[75] Inventor: André Esanu, Paris, France

[73] Assignee: Societe de Conseils de Recherches et d'Applications Scientifiques, France

[21] Appl. No.: 22,620

[22] Filed: Mar. 4, 1987

Related U.S. Application Data

[63] Continuation of Ser. No. 730,788, May 3, 1985, abandoned.

[30] Foreign Application Priority Data

May 11, 1984 [GB] United Kingdom ............... 8412094

[51] Int. Cl.$^4$ ..................... A61K 31/47; C07D 215/18
[52] U.S. Cl. ..................................... 514/312; 546/156
[58] Field of Search ........................ 546/156; 514/312

[56] References Cited

U.S. PATENT DOCUMENTS

| | | | |
|---|---|---|---|
| 4,146,625 | 3/1979 | Lee | 546/156 |
| 4,264,604 | 4/1981 | Sturm | 546/156 |
| 4,327,101 | 4/1982 | Mushika | 546/156 |

Primary Examiner—Robert J. Warden
Assistant Examiner—Robert Benson
Attorney, Agent, or Firm—Lucas & Just

[57] ABSTRACT

The invention relates to new quinoline derivatives of the formula:

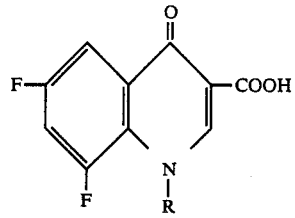

wherein R stands for $C_2H_5$, $C_2H_4F$, $CH_2-O-CH_2-CH_2OH$,

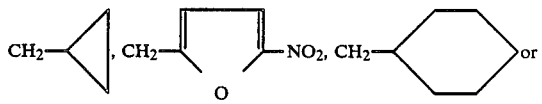

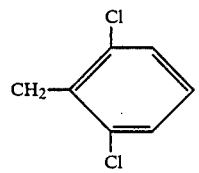

to a process for their preparation comprising reacting, for 12-24 hours, at 70°-95° C., in dimethylformamide, the 1,4-dihydro- 3-ethoxycarbonyl- 6,8- difluoro-4-oxo-quinoline with an excess of RX (2-5 mol of RX for one mol of quinoline), in the presence of $K_2CO_3$ and subsequently hydrolyzing the obtained 3-ester by HCl under reflux conditions and to pharmaceutical compositions comprising at least one 1,4-dihydro- 3-carboxy- 6,8-difluoro- 1-R-4-oxo-quinoline derivative in admixture with a pharmaceutically acceptable diluent or carrier.

2 Claims, No Drawings

NEW QUINOLINE DERIVATIVES, THEIR PREPARATION AND THERAPEUTIC COMPOSITIONS CONTAINING THE SAME

This is a continuation of application Ser. No. 730,788, filed May 3, 1985, now abandoned.

The invention relates to new quinoline derivatives to a process for their preparation and to pharmaceutical compositions containing the same.

The invention provides 1,4-dihydro-3-carboxy-6,8-difluoro-4-oxo-quinolines which have the formula:

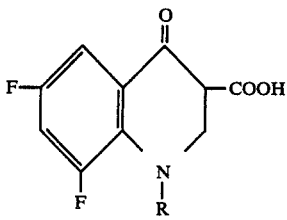

wherein R stands for $C_2H_5$, $C_2H_4F$, $CH_2$—O—$CH_2$—$CH_2OH$,

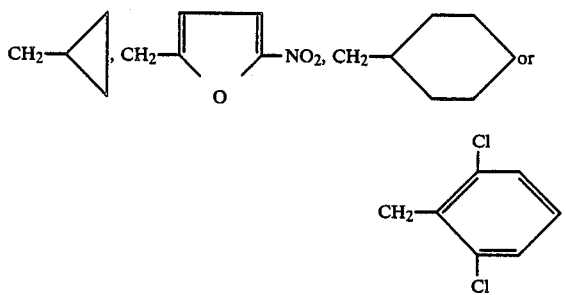

These compounds belong to a rather important group of quinoline derivatives, some of which are known to possess antibacterial activity whereas most of them are completely inactive. In various searches effected in this group of derivatives it has been commonly found that if a product with a certain substituent in a determined position possesses an antibacterial activity, minor changes in the nature of the substituent or in the position generally lead to completely inactive products. For this reason it is completely impossible to forecast whether a particular compound would be active or inactive. The compounds of the invention have been found to have an antibacterial power against a large family of bacteria, either of gram positive or of gram negative nature.

The compounds according to the present invention may easily be prepared starting from 2,4-difluoroaniline. This is condensed with diethyl ethoxymethylenemalonate which leads to 1-(2,2-diethoxycarbonyl-vinylamino)-2,4-difluoro-benzene. This is cyclised by warming to give 1,4-dihydro-3-ethoxycarbonyl-6,8-difluoro-4-oxo-quinoline, which is reacted with RX (X is Cl, Br or I) to attach the corresponding R group to the nitrogen atom. Finally the 1,4-dihydro-3-ethoxycarbonyl-6,8-difluoro-1-R-4-oxo-quinoline is hydrolysed by treatment with hydrochloric acid. This process, which is within the scope of the invention is illustrated by the following reaction scheme;

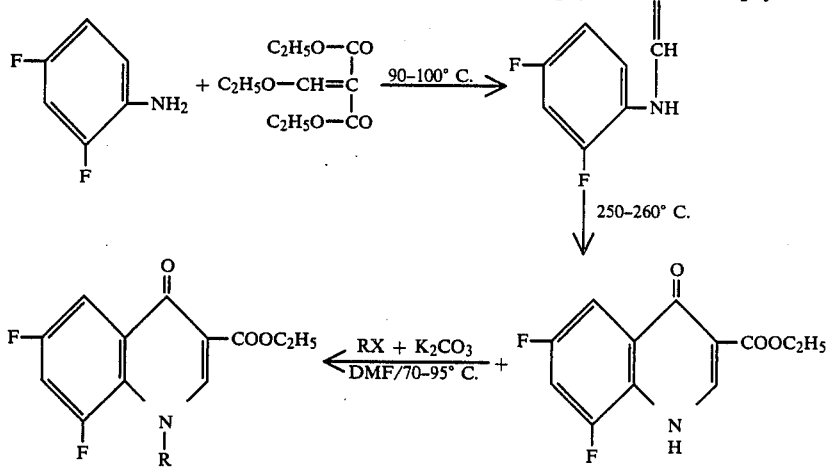

The hydrochloric acid treatment of the obtained compound gives the compound I.

Accordingly the invention relates also to a preparation process of said compounds comprising reacting for 12-24 hours at 70°-95° C., in dimethylformamide the 1,4-dihydro-3-ethoxycarbonyl-6,8-difluoro-4-oxoquinoline with an excess of RX (2-5 mol of RX for one mol of quinoline), in the presence of $K_2CO_3$ and subsequently hydrolysing the obtained 3-ester by HCl under reflux conditions.

The invention finally relates to pharmaceutical compositions comprising at least one 1,4-dihydro-3-carboxy-6,8-difluoro-1-R-4-oxo-quinoline derivative in admixture with a pharmaceutically acceptable diluent or carrier.

The invention is illustrated by the following examples:

EXAMPLE 1

$R = C_2H_5$

Into an appropriate reactor fitted with warming, cooling and stirring means, were poured 152.5 ml (1.5 mol) of 2,4-difluoroaniline and 425 ml (2.1 mol) of diethyl ethoxymethylenemalonate. The mixture was warmed at 90° to 100° C. for about three hours with evacuation of ethanol appearing in the condensation. This led to a solid product which was treated with hexane, washed, crystallized from hexane and dried to give 356.5 g (yield 79.5%) of 1-(2,2-diethoxycarbonyl-vinylamino)-2,4-difluoro-benzene. Elemental analysis of the product showed a good correspondence with the formula $C_{14}H_{15}NO_4F_2$. 350 g (1.17 mol) of this product were poured into a reactor with 1 liter of diphenyloxide. The mixture was refluxed at 265°–270° C. for 1½ hours with a subsequent evacuation of the ethanol produced during the cyclisation. After cooling to ambient temperature, there was obtained a residue which was treated with benzene and then with hexane, dried and recrystallized from methanol. This gave 239 g (yiel 80.7%) of 1,4-dihydro-3-ethoxycarbonyl-6,8-difluoro-4-oxo-quinoline, elemental analysis of which showed a good correspondence with the formula $C_{12}H_9NO_3F_2$.

For the fixation of an ethyl group on the nitrogen atom, 210 g (0.84 mol) of this product, 287 g (2.1 mol) of potassium carbonate and 337 ml (4.2 mol) of ethyl iodide were treated for 24 hours at about 90° C. in the presence of 1.5 liters of dimethylformamide. After evacuation of the dimethylformamide under reduced pressure, the mixture was treated with 1 liter of water and stirred at about 0° C. The resultant precipitate was washed with water, dried and recrystallized from isopropanol at the boil. After separation and drying there were obtained 220 g (yield 93.2%) of 1,4-dihydro-3-ethoxycarbonyl-6,8-difluoro-1-ethyl-4-oxo-quinoline, elemental analysis of which showed a good correspondence with the formula $C_{14}H_{13}NO_3F_2$.

To obtain the corresponding acid, 210 g (0.74 mol) of this product was treated with 2N hydrochloric acid under reflux. This gave 179 g (yield 95%) of 1,4-dihydro-3-carboxy-6,8-difluoro-1-ethyl-4-oxo-quinoline, elemental analysis of which showed a good correspondence with the formula $C_{12}H_9NO_3F_2$. This compound is insoluble in water but soluble in dimethylsulfoxide.

As for the other substituents, the same process is used, their preparation will not be described in details; only the starting material and the characteristics of the compounds will be given.

EXAMPLE 2

$R=C_2H_4F$

Starting material RX was $ClCH_2-CH_2F$. Yields 90.3% (condensation) and 96.2% (hydrolysis) in a white powder melting with sublimation at 268° C. (Tottoli), the analysis of which showed a perfect correspondence with the formula $C_{12}H_8F_3NO_3$. This compound is insoluble in water and in dimethylsulfoxide.

EXAMPLE 3

$R=CH_2-O-CH_2-CH_2-OH$

Starting material RX was

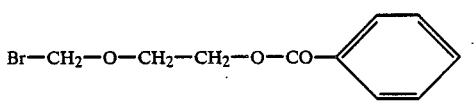

for practical reasons and the benzoxy moiety was hydrolysed together with the 3-ester in the HCl treatment. Yields 56% (condensation) and 73.5% (hydrolysis) in a white powder melting at 218° C. (Tottoli) the analysis of which showed a good correspondence with the formula $C_{13}H_{11}F_2NO_5$. This compound is insoluble in water but soluble in dimethylsulfoxide.

EXAMPLE 4

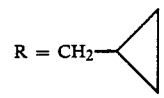

Starting material RX was

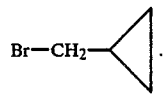

Yields 67% (condensation) and 88.4% (hydroxylsis) in a white powder melting at 204° C. (Tottoli) the anaylis of which showed a perfect correspondence with the formula $C_{14}H_{11}F_2NO_3$. This compound is insoluble in water but soluble in dimethylsulfoxide.

EXAMPLE 5

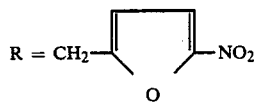

Starting material RX is

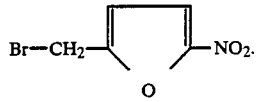

Yields 58% (condensation) and 77% (hydrolysis) in a beige powder melting at 210°–215° C. (Tottoli), the analysis of which showed a perfect correspondence with the formula $C_{15}H_8F_2N_2O_6$. This compound is insoluble in water but soluble in dimethylsulfoxide.

EXAMPLE 6

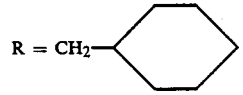

Starting material RX is

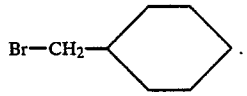

Yields 44% (condensation) and 76% (hydrolysis) in a white powder melting at 241° C. (Tottoli), the analysis of which showed a perfect correspondence with the formula $C_{17}H_{16}F_2NO_3$. This compound is insoluble in water and in dimethylsulfoxide.

EXAMPLE 7

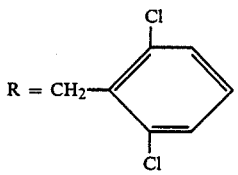

Starting material RX is

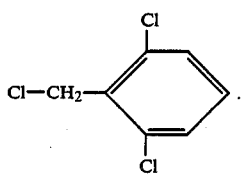

Yields 50% (condensation) and 86.6% (hydrolysis) in a white powder melting at 272° C. (Tottoli), the analysis of which showed a perfect correspondence with the formula $C_{17}H_9Cl_2F_2NO_3$. This compound is insoluble in water and in dimethylsulfoxide.

TOXICITY

The toxicity of the compounds of the invention has been determined per os, by the usual methods on rats and mice. $LD_{50}$ values were from 1320 to 1940 mg/kg on rats and from 910 to 1430 mg/kg on mice.

Usual tests for checking mutagenesis and clastogenesis (Ames test, micronucleus test and lymphocytes cultures) were negative.

BACTERIOLOGY (A) The bactericidal activity of the compounds of the invention has been determined on various microorganisms, as hereinafter described.

Serial dilutions of the test and reference compounds are prepared in Brain Heart Infusion Broth (Oxoid CM225) in two-fold steps from 1000 μg/ml down to 0.5 μg/ml.

The test organisms are cultured on Tryptone Soy Agar (TSA, Oxoid CM131) and checked for viability and purity. Standardized inocula are then ppepared by inoculating slopes of TSA and incubating at 37° C. for 24 hours. The resultant bacterial growth is then removed by the addition of sterile physiological saline and shaking with glass beads. The suspensions of organisms are then standardized to give 50% transmission at 520 nM on an SP600 Spectrophotometer. Calibration curves show this to yield approximately $10^8$ colony forming units per ml.

0.1 ml aliquots of these suspensions are then used to inoculate each of the prepared serial dilutions of the compounds in Brain Heart Infusion Broth.

The sets of dilutions are incubated at 37° C. for 24 hours and then inspected for the presence or absence of growth as shown by turbidity of the medium. The lowest concentration showing no growth of the test organism is recorded as the Minimal Inhibitory Concentration (MIC) of the compound for that organism.

Each of the tubes showing no growth are then subcultured onto plates of Tryptone Soy Agar and incubated at 37° C. for 24 hours. The plates are then inspected for the presence or absence of growth at the inoculation points. The lowest concentration of the test compound which shows no growth on sub-culture is recorded as the Minimal Microbiocidal Concentration (MMC). MIC and MMC are expressed in μg/ml.

The results are presented in the following table, in comparison with those for two reference compounds, nitrofuroxazide and pipemidic acid. The abreviations used in the table have the following meanings:
S.a.: *Staphylococcus aureus* ATCC 6538
S.p.: *Streptococcus pyogenes* NCTC 8198
P.a.: *Pseudomonas aeruginosa* ATCC 9027
E.c.: *Escherichia coli* NCTC 8196
P.m.: *Proteus mirabilis* NCTC 8559
S.e.: *Salmonella enteritidis* NCTC 6676
S.b.: *Shigella boydii* NCTC 9328
Nif.: Nifuroxazide
Pip.: Pipemidic acid
T.M.: Tested microorganism (B) The bacteriostatic activity of the compounds of the invention has also been searched against microorganisms more particularly related with gastro-enteritis.

This experiment was conducted in Mueller—Hinton gelose with tested compounds dissolved in dimethylsulfoxide (control dimethylsulfoxide was provided) at increasing concentrations from 0.01 to 100 μg. The strains used were *Vibrio Cholerae* (3 strains respectively from Europe, Africa and Conth-East-Asia), *Vibrio parahemolyticus*, *Vibrio alginolyticus*, *Aeromonas hydrophila Sobria* and *Salmonella*. Minimum inhibitory concentration was found for the 7 compounds of the invention, between 0.5 and 1 μg for the Salmonella strain and between 0.1 and 0.5 μg for the other strains, which denotes a strong bacteriostatic activity.

(C) This experiment was completed by an in vivo test on batches of each 10 SWISS mice weighing about 20 g and administered orally with the compounds of the invention. Three doses were used for each compound and the urines of each batch were collected for evaluation of their bactericidal activity on cultures of *Vibrio Cholerae* Ogawa ($10^6$ per ml) on Mueller—Hinton gelose. The activity was appreciated, after a 24 hours incubation at 37° C., by the diameter in mm of the inhibition of the strain around the point of introduction in the gelose. A negative control (Nifuroxazide) and a positive control (Pipemidic acid) were used as references. The doses administered to mice were 0.5, 1 and 2.5 μg for the compounds of examples 1 to 5 and 1, 2.5 and 5 μg for the compounds of examples 6 and 7 which appeared less active in preceding experiment.

In this experiment the activity of the compounds of the invention was found at about 1 μg for the compounds of examples 1 to 5 and between 1 and 2.5 μg for the compounds of examples 6 and 7.

PRESENTATION—POSOLOGY

In human therapy the compounds of the invention may be presented in tablets of gelatine capsules, containing 0.1 to 0.5 g of active ingredient per dose unit, for oral administration. Usual posology is 0.5 to 2 g per diem.

Injectable forms include phials of each 0.1 g of active ingredient to be suspended extemporeanously before injection. Posology: 1 to 3 phials per diem.

TABLE

| Compound | T.M. | S.a | S.p. | P.a. | E.c. | P.m. | S.e. | S.b. |
|---|---|---|---|---|---|---|---|---|
| Nif. | MIC | 8 | 1 | 500 | 4 | 500 | 500 | 8 |
|  | MMC | 8 | 1 | 500 | 4 | 500 | 500 | 8 |
| Pip. | MIC | 2 | 4 | 1 | 4 | 4 | 4 | 4 |

TABLE-continued

| Compound | T.M. | S.a | S.p. | P.a. | E.c. | P.m. | S.e. | S.b. |
|---|---|---|---|---|---|---|---|---|
|  | MMC | 250 | 125 | 16 | 4 | 8 | 8 | 4 |
| 1 | MIC | 32 | 16 | 32 | 8 | 1 | 2 | 1 |
|  | MMC | 32 | 32 | 64 | 8 | 2 | 4 | 1 |
| 2 | MIC | 4 | 32 | 8 | 32 | 4 | 4 | 8 |
|  | MMC | 8 | 32 | 8 | 32 | 8 | 8 | 16 |
| 3 | MIC | 4 | 2 | 8 | 4 | 32 | 32 | 8 |
|  | MMC | 8 | 4 | 16 | 8 | 32 | 32 | 8 |
| 4 | MIC | 64 | 4 | 8 | 64 | 1 | 2 | 32 |
|  | MMC | 64 | 4 | 16 | 64 | 2 | 4 | 32 |
| 5 | MIC | 16 | 8 | 2 | 64 | 16 | 125 | 32 |
|  | MMC | 64 | 32 | 2 | 64 | 32 | 125 | 32 |
| 6 | MIC | 8 | 16 | 4 | 64 | 8 | 4 | 8 |
|  | MMC | 16 | 16 | 8 | 64 | 8 | 4 | 8 |
| 7 | MIC | 8 | 32 | 8 | 1 | 2 | 2 | 16 |
|  | MMC | 8 | 64 | 8 | 2 | 4 | 4 | 32 |

I claim:

1. Quinoline compounds of the formula:

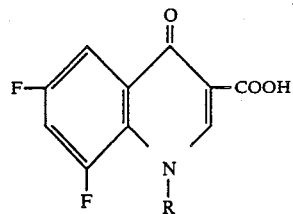

wherein R stands for $C_2H_4F$, $CH_2-O-CH_2-CH_2OH$,

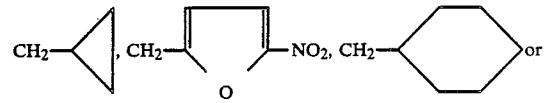

or

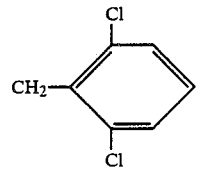

2. Antibacterial compositions comprising at least one 1,4-dihydro-3-carboxy-6,8-difluoro-1-R-4-oxo-quinoline compound of claim 1 in admixture with a pharmaceutically acceptable diluent or carrier.

* * * * *